(12) United States Patent
Aramaki et al.

(10) Patent No.: US 10,765,845 B2
(45) Date of Patent: Sep. 8, 2020

(54) MEDICAL TUBE

(71) Applicant: TERUMO KABUSHIKI KAISHA, Tokyo (JP)

(72) Inventors: Naoki Aramaki, Kanagawa (JP); Yuuki Souma, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 399 days.

(21) Appl. No.: 15/693,964

(22) Filed: Sep. 1, 2017

(65) Prior Publication Data

US 2018/0064918 A1    Mar. 8, 2018

(30) Foreign Application Priority Data

Sep. 2, 2016    (JP) ................ 2016-172142

(51) Int. Cl.
*A61M 27/00* (2006.01)
*A61M 39/24* (2006.01)
*A61M 1/00* (2006.01)
*A61M 25/00* (2006.01)
(Continued)

(52) U.S. Cl.
CPC .......... *A61M 27/002* (2013.01); *A61M 1/008* (2013.01); *A61M 1/0035* (2014.02); *A61M 25/003* (2013.01); *A61M 25/0075* (2013.01); *A61M 39/24* (2013.01); *A61B 17/1114* (2013.01); *A61B 2017/1132* (2013.01); *A61M 1/0003* (2013.01); *A61M 25/065* (2013.01); *A61M 2039/242* (2013.01); *A61M 2039/2433* (2013.01); *A61M 2210/1042* (2013.01)

(58) Field of Classification Search
CPC .............. A61M 27/002; A61M 27/006; A61M 27/008; A61M 1/0003; A61M 1/0035; A61M 1/008; A61M 25/003; A61M 25/0075; A61M 39/24; A61M 2039/242; A61M 2039/2433; A61M 2210/1042; A61B 17/1114; A61B 2017/1132
See application file for complete search history.

(56) References Cited

U.S. PATENT DOCUMENTS 5,019,102 A * 5/1991 Hoene ............... A61M 25/0069
604/264
5,664,567 A * 9/1997 Linder .............. A61M 16/0477
128/207.18
(Continued)

FOREIGN PATENT DOCUMENTS

JP    4715504    7/2007

*Primary Examiner* — Philip R Wiest
(74) *Attorney, Agent, or Firm* — Thaine Lennox-Gentle; Sheridan Ross, PC

(57) ABSTRACT

A medical tube 10 (drain tube 10) includes a main shaft tube 20, a flow path opening/closing mechanism 40, and a branch tube 30. The main shaft tube 20 internally has a main shaft side distal opening 21a and a main shaft lumen 21. The flow path opening/closing mechanism 40 brings the main shaft lumen 21 into a communicating state by applying pressure smaller than predetermined pressure, and brings the main shaft lumen 21 into a blocked state by applying pressure equal to or greater than the predetermined pressure. The branch tube 30 promotes a pancreatic juice pj to flow into a branch lumen 31, based on the applied pressure which is equal to or greater than the predetermined pressure.

20 Claims, 11 Drawing Sheets

(51) Int. Cl.
*A61B 17/11* (2006.01)
*A61M 25/06* (2006.01)

(56) References Cited

U.S. PATENT DOCUMENTS

| | | | | |
|---|---|---|---|---|
| 2013/0325103 A1* | 12/2013 | Arai | ................ | A61F 2/2418 |
| | | | | 623/1.24 |
| 2016/0074622 A1* | 3/2016 | Arai | ................ | A61M 25/0075 |
| | | | | 604/31 |
| 2017/0136209 A1* | 5/2017 | Burnett | ................ | A61M 1/008 |

* cited by examiner

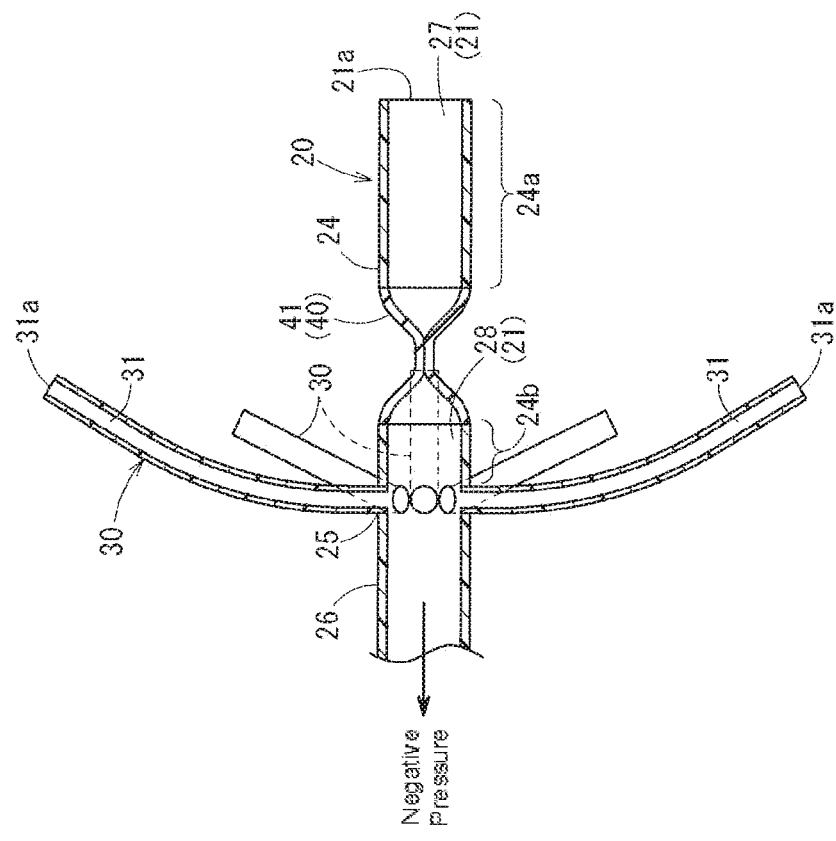
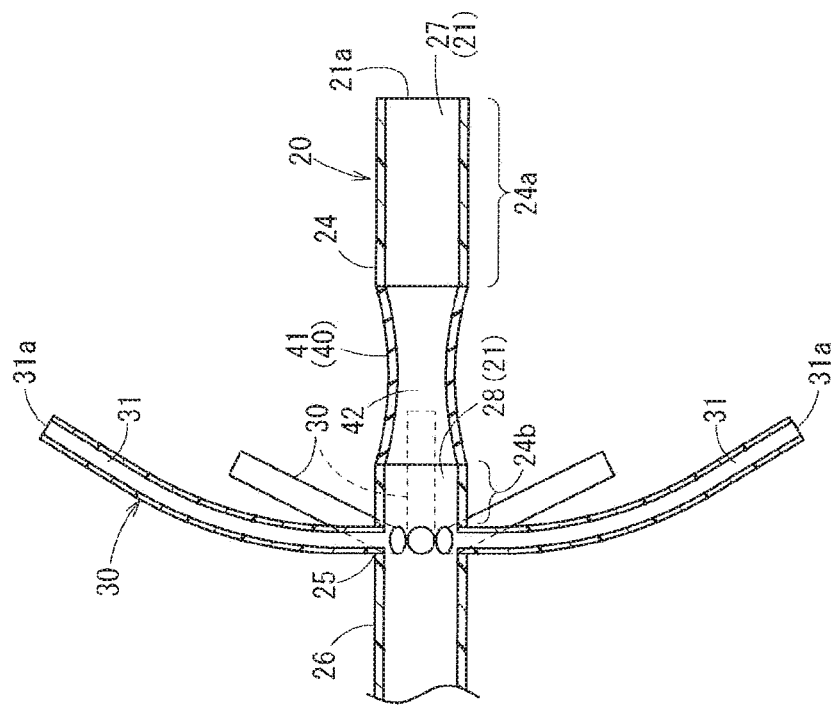

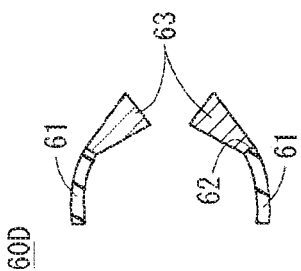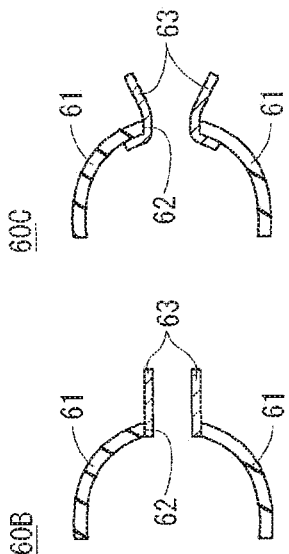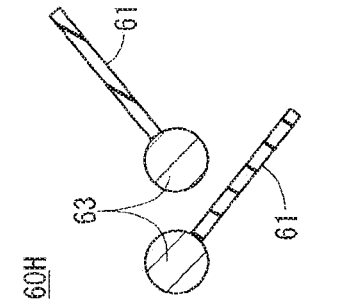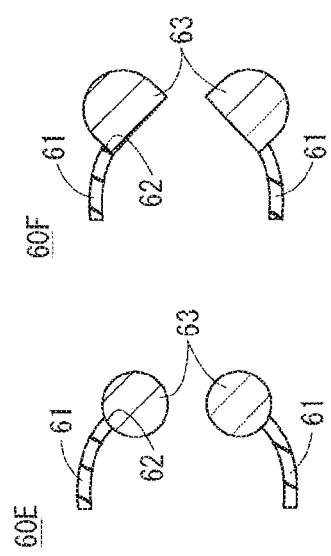

MEDICAL TUBE

CROSS REFERENCE TO RELATED APPLICATIONS

The present application claims the benefit of priority, under 35 U.S.C. § 119(e), to Japanese Application No. 2016-172142, filed Sep. 2, 2016, entitled "Medical Tube", the entire disclosure of which is incorporated herein by reference in its entirety, for all that it teaches and for all purposes.

TECHNICAL FIELD

The present invention relates to a medical tube used for draining a fluid outward from the inside of a living body while indwelling the inside of the living body, for example.

BACKGROUND

After surgery, to drain a fluid (liquid or gas generated by biological tissues or used for treatment) outward from the inside of a body, a medical drain tube (medical tube) as disclosed in Japanese Patent Application No. 4715504 is used.

As an example, in the pancreaticoduodenectomy, the medical drain tube is used for an anastomosis portion where the pancreas (pancreatic body and pancreatic tail) having the excised pancreatic head and the jejunum are anastomosed with each other. A trunk portion of the medical drain tube is caused to indwell after passing through the jejunum, and a distal portion of the medical drain tube is inserted into and caused to indwell the pancreas (main pancreatic duct), which is anastomosed with the jejunum. In this manner, the pancreatic juice generated inside the pancreas is drained out of the body through the medical drain tube from the main pancreatic duct.

SUMMARY

Problem Solved

Incidentally, in a case where a plurality of biological organs is anastomosed with (connected to) each other by performing a surgery, there is a possibility that the fluid generated by the biological organs may leak to a boundary portion between the biological organs. For example, in the anastomosis portion where the pancreas and the jejunum are anastomosed with each other by means of the pancreaticoduodenectomy, the pancreatic juice leaks out from the pancreas side. If the pancreatic juice further leaks from the anastomosis portion into the abdominal cavity, the enzyme contained in the liquid may be activated, in some cases. In this case, there is a possibility that a patient may be adversely affected after the surgery.

The embodiments herein are made to solve the above-described problem, and an object thereof is to provide a medical tube which can drain a fluid contained inside a biological organ and a fluid contained in a boundary portion which connects a plurality of biological organs to each other, and which can promote drain of the fluid contained in the boundary portion if necessary.

Problem Solved

To achieve the above-described object, there is provided a medical tube including an elongated main shaft tube that has a distal end and a proximal end, that has a distal opening on a distal side, and that internally has a lumen which communicates with the distal opening, a lateral introduction portion that is disposed at an intermediate position in an axial direction of the main shaft tube, and that introduces a fluid to the lumen from a boundary portion which connects a plurality of biological organs to each other, and a flow path opening/closing mechanism that is operable to be in a state of opening the lumen and to be in a state of closing the lumen. The flow path opening/closing mechanism closes the lumen, when negative pressure is applied to the lumen on a proximal side further from flow path opening/closing mechanism, and opens the lumen, when positive pressure is applied to the lumen on a distal side further from the flow path opening/closing mechanism or when the negative pressure is released. The fluid is aspirated into the lumen via the lateral introduction portion by the negative pressure, and flows inside the main shaft tube in a proximal end direction.

According to the above-described configuration, the medical tube has the flow path opening/closing mechanism. Accordingly, the positive pressure is applied to the lumen on the distal side further from the flow path opening/closing mechanism, or application and non-application (release) of the negative pressure are changed therebetween on the proximal side further from the flow path opening/closing mechanism. Therefore, the lumen of the main shaft tube can be switched between a closed state and an open state. In this manner, in the open state of the flow path opening/closing mechanism, the fluid flowing from the distal opening of the main shaft tube inserted into the biological organ and the fluid flowing from the lateral introduction portion disposed in the boundary portion which connects the plurality of biological organs to each other can be drained after flowing through the lumen in the proximal end direction. In addition, if the flow path opening/closing mechanism is brought into the closed state, it is possible to promote the fluid to flow from the lateral introduction portion. Therefore, the medical tube can more satisfactorily encourage recovery of a patient.

In this case, the lumen can be disposed at one location inside the main shaft tube, and that the flow path opening/closing mechanism is disposed on the distal side further from the lateral introduction portion.

In this manner, the flow path opening/closing mechanism can switch opening/closing of the lumen on the distal side further from the lateral introduction portion. Therefore, if the flow path opening/closing mechanism is closed by the applied negative pressure, it is possible to further promote the fluid to flow from the lateral introduction portion.

In addition, the flow path opening/closing mechanism may be more flexible than a wall portion of the main shaft tube, and both end portions are cylindrical portions fixed to the wall portion, and that the cylindrical portions close the lumen in such a way that the cylindrical portions are deformed so that inner walls thereof come into contact with each other when the negative pressure is applied.

In this way, the flow path opening/closing mechanism is the cylindrical portion. Accordingly, the flow path opening/closing mechanism can be simply manufactured, and can be fixed to a desired position of the main shaft tube. Then, the cylindrical portion is more flexible than the wall portion of the main shaft tube. Accordingly, the cylindrical portion is smoothly bent by the applied negative pressure so that the inner walls come into contact with each other. Therefore, the lumen can be firmly closed.

Alternatively, the flow path opening/closing mechanism may be a diaphragm which is disposed on an inner surface of the main shaft tube configuring the lumen, and which has a port capable of opening/closing the lumen.

In this way, even if the flow path opening/closing mechanism is the diaphragm, the port is closed by the applied negative pressure. Accordingly, the lumen can be satisfactorily switched between a communication state and a blocked state. In addition, the port is opened by the released negative pressure, thereby being capable of causing the lumen to be in the communicating state.

Alternatively, a reinforcement body can be disposed in the port.

In this way, the flow path opening/closing mechanism includes the reinforcement body. Accordingly, the port can be more reliably closed in response to elastic deformation of the diaphragm.

Furthermore, the lumen may be divided into a first lumen communicating with the distal opening and a second lumen communicating with the lateral introduction portion so as to be independent of each other inside the main shaft tube, and the flow path opening/closing mechanism may open/close the first lumen.

In this way, even if the structure is employed in which the lumen is divided into the first lumen and the second lumen, the flow path opening/closing mechanism closes the first lumen. Accordingly, it is possible to promote drain of the fluid flowing in the second lumen from the lateral introduction portion.

In addition to the above-described configurations, the main shaft tube may have a partition wall which partitions the first lumen and the second lumen. The partition wall may have a gas permeable wall which allows gas to permeate and inhibits a liquid from permeating between the first lumen and the second lumen. The flow path opening/closing mechanism may be a deformable wall portion which is disposed at a position facing the gas permeable wall, and which configures a portion of the main shaft tube. The deformable wall portion may close the first lumen by coming into contact with the gas permeable wall when the negative pressure is applied. Then, when the positive pressure is applied to the first lumen or when the negative pressure applied to the second lumen is released, the first lumen is opened.

In this way, the gas permeable wall is disposed on the partition wall. Accordingly, the fluid can be aspirated from the second lumen side via the gas permeable wall so that the deformable wall portion is shrunk inward. In this way, for example, a closing degree of the flow path opening/closing mechanism (balance between the pressure for closing the flow path opening/closing mechanism using the negative pressure and the pressure for opening the flow path opening/closing mechanism using the positive pressure) can be adjusted in accordance with a size of a hole portion on the gas permeable wall through which the gas permeates.

Furthermore, the lateral introduction portion can be at least one branch tube which extends from the main shaft tube, which has a branch side distal opening, and which has the branch lumen communicating with the branch side distal opening.

In this way, the lateral introduction portion is at least one branch tube. Accordingly, the branch tube is disposed between the plurality of biological organs, thereby being capable of satisfactory collecting the fluid generated between the plurality of biological organs.

Advantages of the Embodiments

According to embodiments presented herein, a medical tube can drain a fluid contained inside a biological organ and a fluid contained in a boundary portion which connects a plurality of biological organs to each other, and can promote drain of the fluid contained in the boundary portion if necessary.

BRIEF DESCRIPTION OF THE DRAWINGS

FIG. 3A is a side cross-sectional view illustrating an enlarged distal side of the medical tube in FIG. 1 in accordance with embodiments of the present disclosure;

FIG. 3B is a side cross-sectional view for describing an operation of an interlock cylindrical portion when negative pressure is applied to a main shaft lumen in FIG. 3A in accordance with embodiments of the present disclosure;

FIG. 9A is a schematic cross-sectional view illustrating each flow path opening/closing mechanism in accordance with embodiments of the present disclosure;

FIG. 9B is a schematic cross-sectional view illustrating each flow path opening/closing mechanism in accordance with embodiments of the present disclosure;

FIG. 9C is a schematic cross-sectional view illustrating each flow path opening/closing mechanism in accordance with embodiments of the present disclosure;

FIG. 9D is a schematic cross-sectional view illustrating each flow path opening/closing mechanism in accordance with embodiments of the present disclosure;

FIG. 9E is a schematic cross-sectional view illustrating each flow path opening/closing mechanism in accordance with embodiments of the present disclosure;

FIG. 9F is a schematic cross-sectional view illustrating each flow path opening/closing mechanism in accordance with embodiments of the present disclosure;

FIG. 9G is a schematic cross-sectional view illustrating each flow path opening/closing mechanism in accordance with embodiments of the present disclosure;

FIG. 9H is a schematic cross-sectional view illustrating each flow path opening/closing mechanism in accordance with embodiments of the present disclosure;

DETAILED DESCRIPTION

Hereinafter, embodiments of a medical tube will be described in detail with reference to the accompanying drawings.

Figure 1:
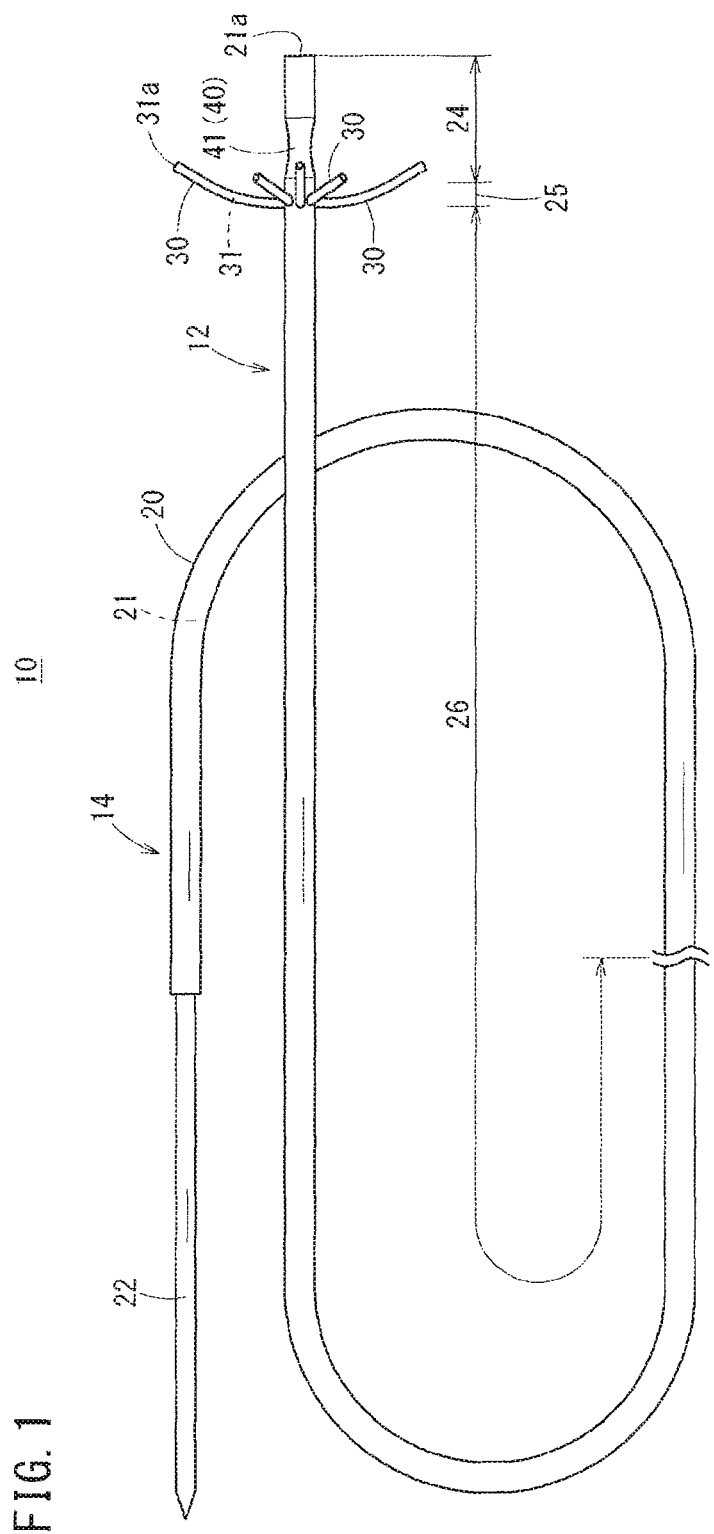
FIG. 1 is a side view illustrating an overall configuration of a medical tube in accordance with embodiments of the present disclosure.

A medical tube 10 in accordance with embodiments of the present disclosure is formed in a hollow tube as illustrated in FIG. 1, and is configured to serve as a medical device through which a fluid (liquid or gas) can flow. In particular, the medical tube 10 is used as a drainage tube in which a distal portion side is caused to indwell a connection section of two biological organs inside a living body so that the fluid generated by (exuded from or secreted by) the biological organ flows and is drained to a proximal portion side exposed outward from the body. Accordingly, hereinafter, the medical tube 10 is referred to as a drain tube 10.

Figure 2A:
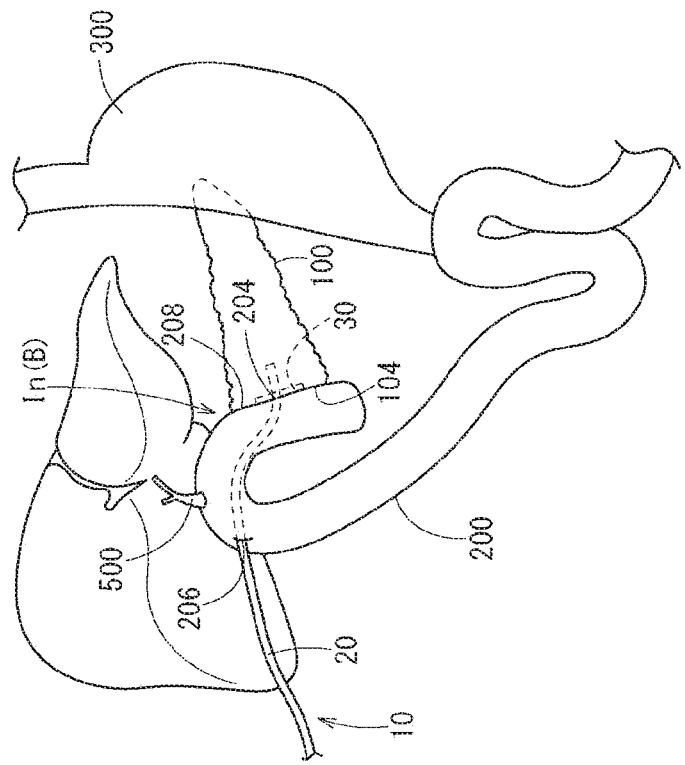
FIG. 2A is a first description-purpose view illustrating a flow in the pancreaticoduodenectomy in accordance with embodiments of the present disclosure.
Figure 2B:
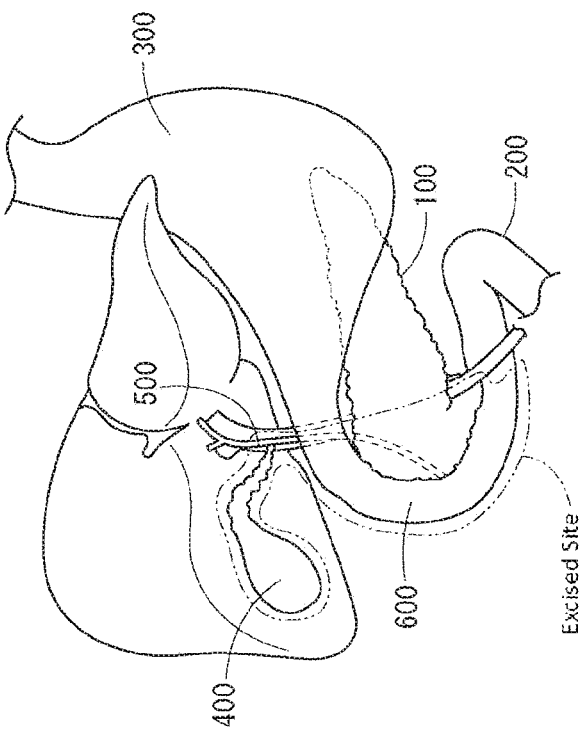
FIG. 2B is a second description-purpose view illustrating a reconstructed state of an organ in the pancreaticoduodenectomy in accordance with embodiments of the present disclosure.

For example, as illustrated in FIGS. 2A and 2B, the drain tube 10 is applicable to a reconstructive surgery of an organ in the pancreaticoduodenectomy (including the pyloruspreserving pancreaticoduodenectomy). The pancreaticoduodenectomy is a surgery for cutting off a pancreatic head side of a pancreas 100, a portion of a stomach 300, a gall bladder 400, a bile duct 500, and a duodenum 600 in order to treat symptoms such as the pancreatic head cancer, the chronic pancreatitis, the bile duct cancer, the duodenal cancer, and the duodenal papillary carcinoma. As the reconstructive surgery, the end side pancreaticojejunostomy is performed. When the end side pancreaticojejunostomy is performed, in the drain tube 10, a distal portion side is caused to indwell the inside of the pancreas 100 which is a first biological organ, and a trunk portion is exposed outward from the body after passing through the inside of the jejunum 200 which is a second biological organ. In this manner, a pancreatic juice (fluid) generated from the pancreas 100 after surgery is drained outward from the body.

The pancreatic juice contains an enzyme (amylase) which decomposes proteins, fats and saccharides. In a case where the pancreatic juice leaks into an abdominal cavity, there is a possibility that the activated enzyme may cause serious complications (pancreatic fistula: for example, intraperitoneal hemorrhage, sepsis, peritonitis, or abdominal abscess). The drain tube 10 drains the pancreatic juice generated from the reconstructed pancreas 100 outward from the body, and restrains the pancreatic juice from leaking into the abdominal cavity. In particular, the drain tube 10 can function to cause the pancreatic juice leaking out to a boundary portion B of an anastomosis portion In(B) (connection section) between the pancreas 100 and the jejunum 200 to be drained outward from the body. Hereinafter, a configuration of the drain tube 10 will be described in detail.

As illustrated in FIG. 1, the drain tube 10 includes an insertion planned region 12 to be inserted into the body and an exposure planned region 14 exposed outward from the body, which are consecutively disposed in the axial direction. The total length (axial length) of the drain tube 10 is not particularly limited. However, for example, the length is 500 mm to 1,000 mm.

Specifically, the drain tube 10 has an elongated main shaft tube 20, that configures a drain path for draining the fluid, a plurality of branch tubes 30 disposed at an intermediate position in an axial direction of the main shaft tube 20, and an interlock cylindrical portion 41 disposed on the main shaft tube 20 on the distal side further from the branch tube 30. Only one branch tube 30 may be disposed for the main shaft tube 20.

As illustrated in FIGS. 1, 3A, and 3B, a shaft center portion of the main shaft tube 20 has a main shaft lumen 21 through which the fluid can flow. A main shaft side distal opening 21a communicating with the main shaft lumen 21 is disposed in the distal end of the main shaft tube 20. The main shaft tube 20 is configured to be flexible enough so that the main shaft tube 20 can indwell the inside of the body after being moderately deformed, and is configured to be rigid enough so that the main shaft tube 20 does not crush the main shaft lumen 21.

In addition, the main shaft tube 20 extends over the above-described insertion planned region 12 and the above-described exposure planned region 14 while maintaining a constant outer diameter and inner diameter. The outer diameter of the main shaft tube 20 can be in a range of 1.3 mm to 5 mm, for example, so that insertion and indwelling of the main shaft tube 20 can be performed on a main pancreatic duct 102 of the pancreas 100. In addition, the diameter (inner diameter of the main shaft tube 20) of the main shaft lumen 21 can be in a range of 1.0 mm to 4.5 mm, for example. The outer diameter and the inner diameter of the main shaft tube 20 may be changed along the axial direction of the main shaft tube 20.

A guide needle 22 is disposed in the proximal portion of the main shaft tube 20 (exposure planned region 14). The guide needle 22 is configured to include a metal material such as aluminum, for example. The guide needle 22 pierces a small hole opened in the jejunum 200 in a pancreaticojejunostomy planned region, and guides the main shaft tube 20 into the jejunum 200. Thereafter, the guide needle 22 pierces outward from the jejunum lumen at a pulling-out planned position of the main shaft tube 20, and the main shaft tube 20 is pulled out of the jejunum 200. Furthermore, the guide needle 22 pierces into a small excision hole at a tube pulling-out position of the abdominal wall, and the main shaft tube 20 is pulled out of the body. The main shaft tube 20 pulled out of the body is cut at a proper position, and the guide needle 22 is cut off.

Figure 4:
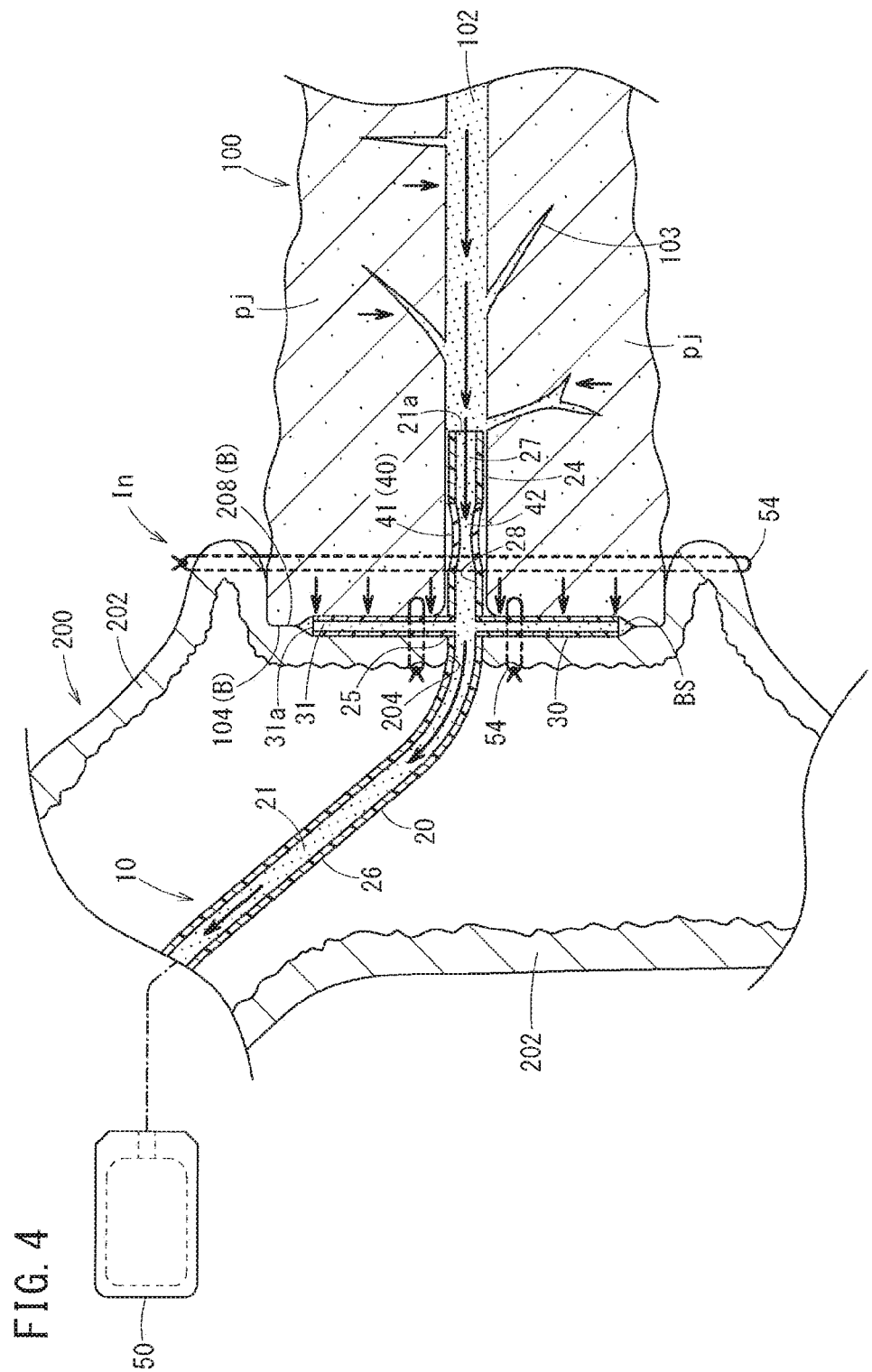
FIG. 4 is a side cross-sectional view illustrating an example where a pancreatic juice is drained in a normal state after the medical tube is applied to an anastomosis portion between the pancreas and the jejunum in accordance with embodiments of the present disclosure.
Figure 5:
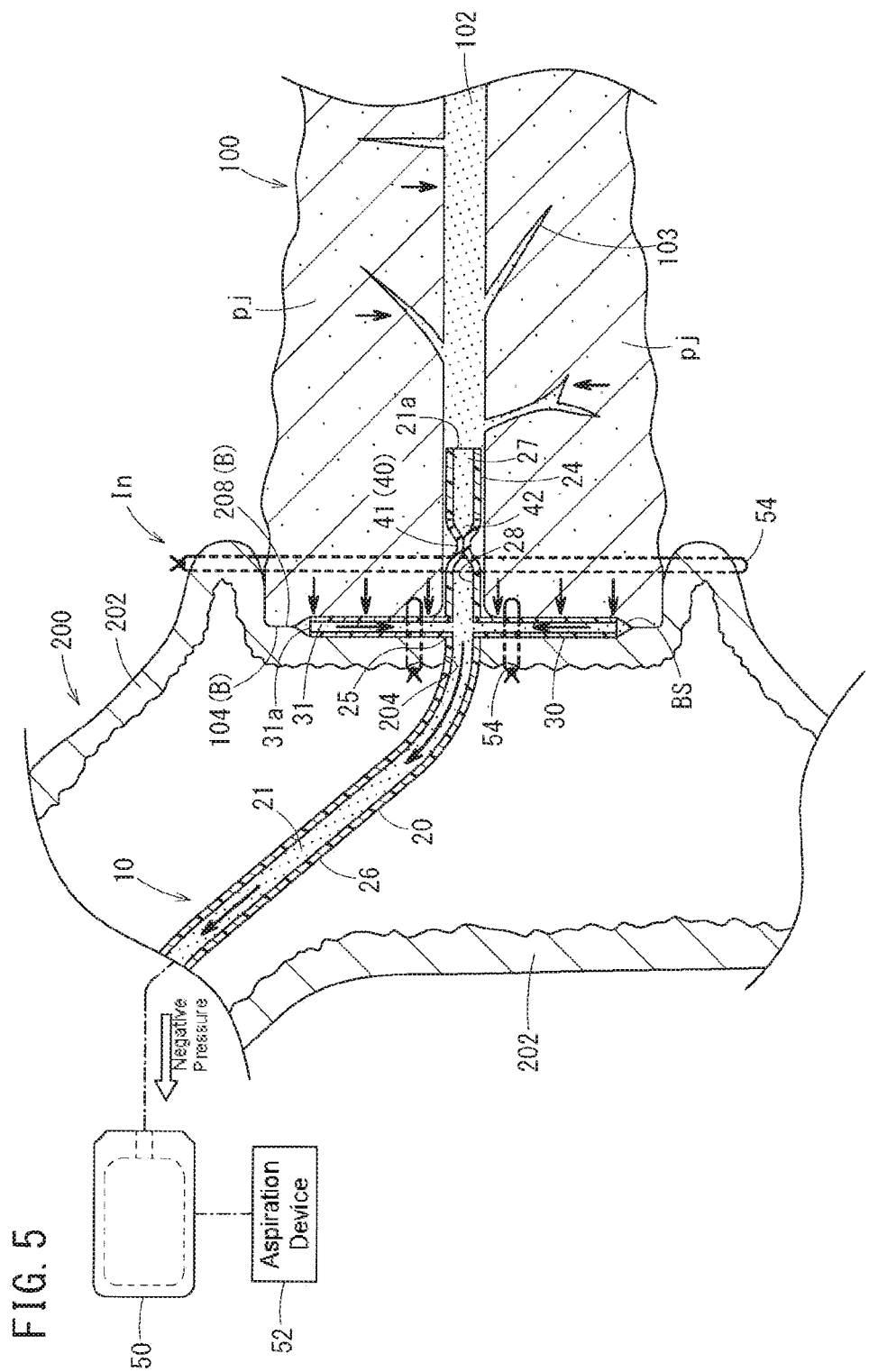
FIG. 5 is a side cross-sectional view illustrating an example where the pancreatic juice is drained in a state where negative pressure is applied after the medical tube is applied to the anastomosis portion between the pancreas and the jejunum in accordance with embodiments of the present disclosure.
Figure 6:
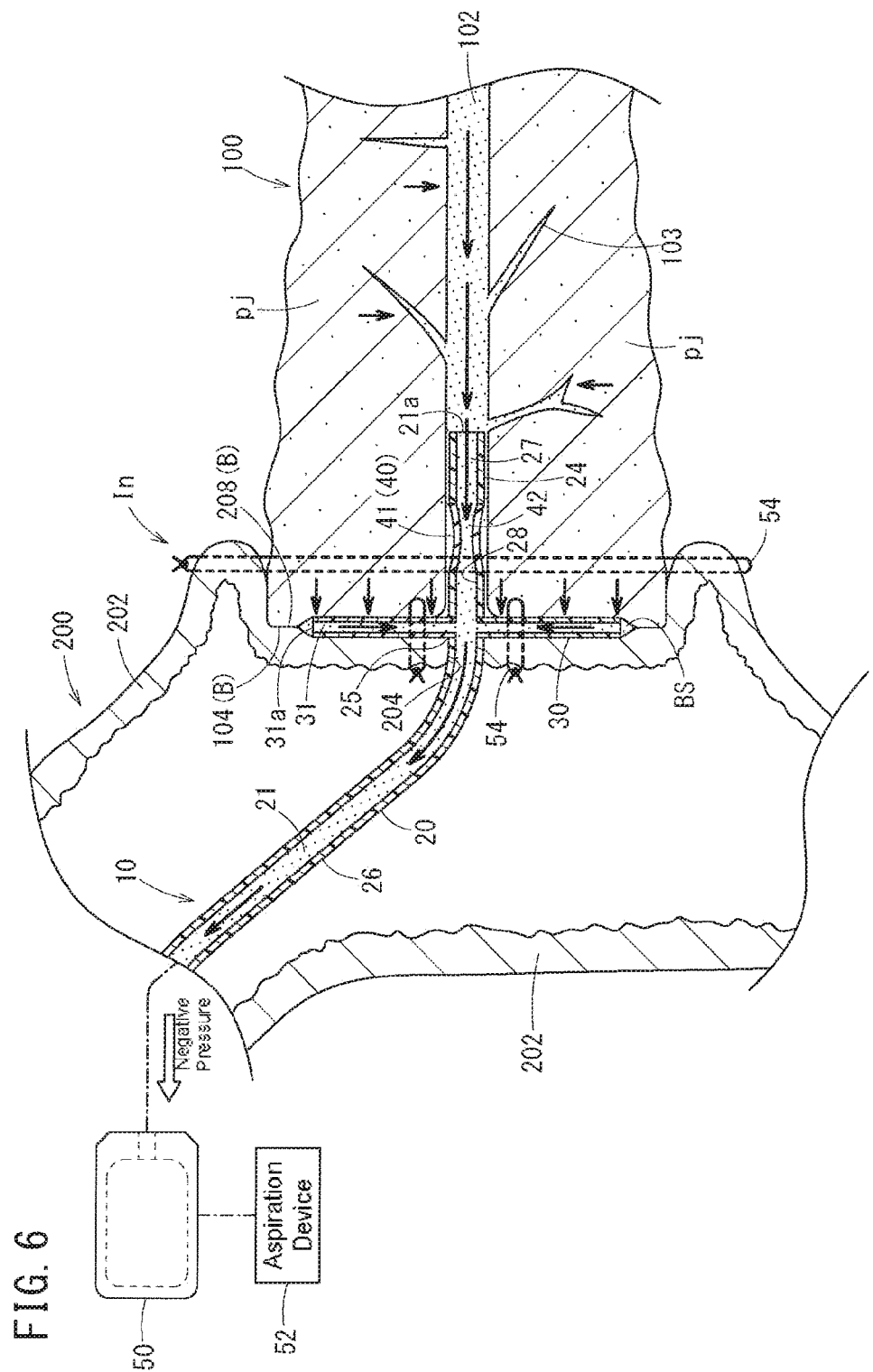
FIG. 6 is a side cross-sectional view illustrating an example where the pancreatic juice is drained in a state where positive pressure is applied after the pancreas secretes the pancreatic juice from the state illustrated in FIG. 5 in accordance with embodiments of the present disclosure.

The proximal side of the main shaft tube 20 which is cut off is connected to a drain bag 50 (including a container which is installed in an aspiration device 52 so as to be capable of applying negative pressure: refer to FIGS. 4 to 6).

The drain bag 50 is set in the aspiration device 52, thereby applying the negative pressure to the main shaft lumen 21 while the aspiration device 52 is operated. For example, the aspiration device 52 is applicable to a mechanism for generating the negative pressure in such a way that a sheet of a contracted bag portion is pulled using a spring so as to expand a space portion of the bag portion.

On the other hand, when the main shaft tube 20 indwells, the insertion planned region 12 of the main shaft tube 20 can be divided into a first site 24 inserted into the pancreas 100, a second site 25 disposed in the boundary portion B of the anastomosis portion In(B), and a third site 26 disposed in the jejunum 200 (including a range where the main shaft tube 20 is removed outward from the jejunum 200 inside the body). The first to the third sites 24, 25, and 26 are continuous in order from the distal end to the proximal end of the main shaft tube 20. In the addition site, the interlock cylindrical portion 41 (cylindrical portion) is disposed on the proximal side of the first site 24, and the plurality of branch tubes 30 interlock with the second site 25.

The main shaft tube 20 may have a fixing mechanism (not illustrated) (for example, a balloon) for fixing the drain tube 10 to the main pancreatic duct 102 or the boundary portion B. In addition, the distal end of the main shaft tube 20 may be formed on a blade surface which is inclined with respect to the shaft center of the main shaft tube 20. In this manner, the main shaft tube 20 is easily inserted into the pancreas 100. Furthermore, the outer peripheral surface of the first site 24 may have a side hole (not illustrated) through which the pancreatic juice is allowed to flow into the main shaft lumen 21.

Furthermore, the main shaft tube 20 can be configured so that the first to third sites 24, 25, and 26 have mutually different hardness. For example, the first and second sites 24 and 25 are hardened compared to the third site 26. In this manner, when the drain tube 10 is removed, it is possible to prevent the first and second sites 24 and 25 from being broken due to the compression of the pancreas 100 or the jejunum 200.

A material configuring the main shaft tube 20 is not particularly limited. However, for example, a resin material can be used. The resin material can include fluorine-based resin, for example one or more of, but not limited to: polytetrafluoroethylene (PTFE), ethylene tetrafluoroethylene copolymer (ETFE), and, perfluoroalkoxy fluorine resin (PFA), olefin-based resin such as polyethylene and polypropylene, or a mixture thereof, polyvinyl chloride, polyurethane, polyester, polyamide, polyether nylon resin, or a mixture of olefin-based resin and ethylene-vinyl acetate copolymer.

On the other hand, the branch tube 30 is configured to serve as a lateral introduction portion which collects the pancreatic juice leaking to the boundary portion B of the anastomosis portion in between the pancreas 100 and the jejunum 200. The eight branch tubes 30 interlock with the outer peripheral surface (in the same axial direction) of the second site 25 of the main shaft tube 20. The respective branch tubes 30 are disposed at equal intervals (at equal angles) along the outer peripheral surface of the main shaft tube 20, and extend radially outward from the main shaft tube 20. In the respective branch tubes 30, the proximal side serves as a fixed end which interlocks with the main shaft tube 20. In contrast, the distal side serves as a free end which is freely displaced with respect to the proximal side. In addition, the eight branch tubes 30 are configured so that the axial lengths thereof are alternately changed (different from each other) along the circumferential direction of the main shaft tube 20.

The shaft center portion of the respective branch tubes 30 has a branch lumen 31 communicating with the main shaft lumen 21. In addition, the distal end of the respective branch tubes 30 has a branch side distal opening 31a with which the branch lumen 31 communicates. The diameter (inner diameter of the branch tube 30) of the branch lumen 31 may be in a range 1.0 mm to 3.3 mm, for example.

Furthermore, the respective branch tubes 30 are formed into a tubular body thinner than the main shaft tube 20 to some extent. For example, the outer diameter of the branch tube 30 depends on the outer diameter of the main shaft tube 20 or the number of the branch tubes 30 to be formed. However, the outer diameter can be equal to or smaller than ½ of the outer diameter of the main shaft tube 20.

In addition, as illustrated in FIG. 3A, the plurality of branch tubes 30 are shaped in advance so as not only to face outward in the radial direction of the main shaft tube 20, but also to extend from the intermediate position in the axial direction to the first site 24 side (distal side) of the main shaft tube 20. Furthermore, the respective branch tubes 30 are configured to be more flexible than the main shaft tube 20.

A material for configuring the plurality of branch tubes 30 is not particularly limited. However, for example, the resin material used for the above-described main shaft tube 20 may be applicable. In this case, if the main shaft tube 20 and the branch tube 30 are formed of the same material and molded integrally with each other, the drain tube 10 is easily manufactured, and the second site 25 of the main shaft tube 20 is provided with improved rigidity. As a matter of course, the drain tube 10 may be configured so that the main shaft tube 20 and the branch tube 30 are separately manufactured and the branch tube 30 is connected to the outer peripheral surface of the main shaft tube 20 after being manufactured.

On the other hand, as illustrated in FIGS. 1, 3A, and 3B, the interlock cylindrical portion 41 is disposed close to the second site 25 in the first site 24, and is configured to serve as a flow path opening/closing mechanism 40 which opens/closes the main shaft lumen 21 in the first site 24.

More specifically, the interlock cylindrical portion 41 is formed in a cylindrical shape internally having an intermediate lumen 42 communicating with the main shaft lumen 21, and the first site 24 is further divided into a distal cylindrical portion 24a and a proximal cylindrical portion 24b. The ring-shaped distal surface of the interlock cylindrical portion 41 is fixed to the ring-shaped proximal surface of the distal cylindrical portion 24a, and the ring-shaped proximal surface of the interlock cylindrical portion 41 is fixed to the ring-shaped distal surface of the proximal cylindrical portion 24b. In addition, the main shaft lumen 21 is also divided into a distal side lumen 27 located in the distal cylindrical portion 24a across the intermediate lumen 42, and a proximal side lumen 28 located in the overall main shaft tube 20 on the proximal side further from the proximal cylindrical portion 24b.

The interlock cylindrical portion 41 is configured to be more flexible (elastic) than the main shaft tube 20. In response to the negative pressure applied from the proximal side of the main shaft lumen 21, the interlock cylindrical portion 41 is deformed so that the inner walls of the interlock cylindrical portion 41 come into contact with each other, thereby closing the main shaft lumen 21.

That is, the interlock cylindrical portion 41 has rigidity (shape maintaining force) for opening the intermediate lumen 42 in a normal state where the main shaft tube 20 is inserted into the pancreas 100 and is under atmospheric pressure (state where the negative pressure is not received from the proximal side lumen 28).

On the other hand, in the interlock cylindrical portion 41, if the drain bag 50 set in the aspiration device 52 applies the negative pressure and the negative pressure acts from the proximal side lumen 28, the inner walls in the inner circumferential direction which configure the interlock cylindrical portion 41 are moved inward so as to be close to each other. The negative pressure applied to the main shaft lumen 21 by the drain bag 50 can be in a range of approximately −30 to −70 mmHg or approximately −45 to −50 mmHg. For example, the interlock cylindrical portion 41 is designed to be elastically deformed inward in a case where the negative pressure applied from the main shaft lumen 21 is −30 mmHg. Therefore, the interlock cylindrical portion 41 opens the intermediate lumen 42 in a normal state, and closes the intermediate lumen 42 if the negative pressure equal to or lower than −30 mmHg acts from the proximal side of the main shaft lumen 21. As a result, in the main shaft lumen 21 (the distal side lumen 27 and the proximal side lumen 28), the communication in the axial direction is blocked (refer to FIG. 5).

Then, when the intermediate lumen 42 is closed by the negative pressure on the proximal side, the pancreatic juice secreted inside the pancreas 100 flows from the main pancreatic duct 102 to the main shaft side distal opening 21a, thereby applying small pressure to the interlock cylindrical portion 41. For example, the pressure is approximately 2 mmHg to 22 mmHg. If the pressure equal to or higher than prescribed pressure is applied by the pancreatic juice, the inner walls in the circumferential direction which configure the interlock cylindrical portion 41 spread outward. In this manner, the pancreatic juice is drained from the distal side lumen 27 through the intermediate lumen 42 to the proximal side lumen 28 (refer to FIG. 6).

If the pancreatic juice is drained in this way and the amount of the pancreatic juice of the distal side lumen 27 decreases, the pressure inside the distal side lumen 27 is lowered. Therefore, the interlock cylindrical portion 41 closes the intermediate lumen 42 again in response to the negative pressure on the proximal side (refer to FIG. 5).

In a state where the negative pressure on the proximal side is applied in this way, the intermediate lumen 42 is opened when the distal side is pressurized, and is closed when the distal side is depressurized. In this manner, the pancreatic juice can be drained without applying the negative pressure as far as possible into the main pancreatic duct 102 into which the main shaft tube 20 is inserted. In addition, the interlock cylindrical portion 41 may open the main shaft lumen 21 by releasing or weakening the negative pressure and by being deformed so as to return to a normal state or a state close to the normal state.

A material configuring the interlock cylindrical portion 41 is not particularly limited. However, for example, the material can include various rubber materials (particularly, sulfurized materials), for example, one or more of, but not limited to: natural rubber, isoprene rubber, butyl rubber, chloroprene rubber, nitrile-butadiene rubber, styrene-butadiene rubber, and silicone rubber, polyolefin such as styrene-based type elastomer, hydrogenated styrene-based elastomer, styrene-based elastomer with polyethylene, polypropylene, polybutene, and α-olefin copolymer, oil such as liquid paraffin and process oil, a mixture of powdered inorganic materials such as talc, cast, and mica, and polyvinyl chloride-based elastomer, olefin-based elastomer, polyester-based elastomer, polyamide-based elastomer, polyurethane-based elastomer, or a mixture thereof.

In a side surface cross-sectional view illustrated in FIG. 3A, as the interlock cylindrical portion 41 in a normal state, a shape is illustrated in which the intermediate portion in the axial direction is slightly slackened inward. However, the shape of the interlock cylindrical portion 41 is not limited thereto. For example, in a side surface cross-sectional view, the interlock cylindrical portion 41 may linearly extend in the axial direction from the main shaft tube 20. In this manner, the pancreatic juice flowing from the main shaft side distal opening 21a is allowed to flow smoothly. In addition, the interlock cylindrical portion 41 may have a bellows shape in which irregularities (waves) are repeatedly formed. Alternatively, the inner surface of the interlock cylindrical portion 41 may have a protruding portion which can promote closing of the intermediate lumen 42 by protruding inward in the radial direction.

The drain tube 10 can be basically configured as described above. Hereinafter, an operation effect will be described.

As described above, the drain tube 10 is used for the pancreaticoduodenectomy. In the pancreaticoduodenectomy, for example, as illustrated in FIG. 2A, a portion of the pancreas 100 (pancreatic head side), the duodenum 600, the gall bladder 400, the bile duct 500, and a portion of the jejunum 200 are excised (refer to a two-dot chain line in FIG. 2A). In addition, although FIG. 2A illustrates a procedure for preserving the pylorus ring of the stomach 300, in the pancreaticoduodenectomy, a portion (pylorus side) of the stomach 300 is also excised if necessary.

Then, as illustrated in FIG. 2B, in the reconstructive surgery (end side pancreaticojejunostomy) of the pancreaticoduodenectomy, an end portion of on the exit side (pylorus side) of the stomach 300 is anastomosed with the intermediate position of the jejunum 200. In addition, the cut-off end portion on the side opposite to the bile duct 500 leading to the liver is anastomosed with the intermediate position of the jejunum 200. Furthermore, the pancreas 100 (pancreatic body and pancreatic tail) is anastomosed with the vicinity of the end portion of the excised jejunum 200. The order of the anastomosis may vary in accordance with a selected operation.

After the anastomosis starts to be performed on the pancreas 100 and the jejunum 200, the drain tube 10 is caused to indwell across the pancreas 100, the boundary portion B between the pancreas 100 and the jejunum 200, and the jejunum 200. Specifically, two ports (first port 204 and second port 206) are formed on an intestinal wall 202 so that the drain tube 10 passes through the inside of the jejunum 200. The first port 204 has a function as a pseudo-Valter's papilla, and the distal side from the second site 25 of the main shaft tube 20 passing through the inside of the jejunum 200 is exposed from the jejunum 200. The second port 206 causes the proximal side (third site 26) of the main shaft tube 20 passing through the inside of the jejunum 200 to be exposed from the jejunum 200. The main shaft tube 20 exposed from the second port 206 is taken out of the body from the inside of the body.

As illustrated in FIG. 4, an operator punctures the first site 24 of the main shaft tube 20, and inserts the main shaft tube 20 into a cut surface 104 of the pancreas 100 before the anastomosis. The first site 24 enters the inside along the main pancreatic duct 102 from the cut surface 104, and the main shaft side distal opening 21a is disposed inside the main pancreatic duct 102. If the first site 24 is substantially inserted into the pancreas 100 and the second site 25 comes close to the cut surface 104, the outer peripheral surface of the branch tube 30 comes into contact with the cut surface 104. At this time, the plurality of branch tubes 30 radially extend outward in the radial direction from the substantially central portion of the cut surface 104 of the pancreas 100 while maintaining mutually different lengths. In this manner, the distal ends (branch side distal opening 31a) are dispersed and disposed in the circumferential direction and the radial direction, respectively.

In this state, the operator disposes the cut surface 104 of the pancreas 100 so as to face and come into surface contact with the intestinal wall 202 around the first port 204 of the jejunum 200 (hereinafter, the outer peripheral surface of the intestinal wall 202 which faces the cut surface 104 is referred to as a facing surface 208). Then, for example, the intestinal wall 202 creates a state where the cut surface 104 of the pancreas 100 and the lateral surrounding connected to the cut surface 104 are covered and reduced in size. The intestinal wall 202 of a portion laterally protruding from the pancreas 100 and the lateral surrounding of the pancreas 100 are sutured using a suture 54. Furthermore, in order to maintain a contact state between the pancreas 100 and the jejunum 200 and to position the branch tube 30, the anastomosis may be performed using the suture 54 by suturing the branch tube 30, the pancreas 100, and the intestinal wall 202. If the suture 54 is configured so that a biodegradable material is employed and is dissolved inside the body during the indwelling, time and efforts for removal can be saved.

Through the above-described anastomosis, in a state where the branch tube 30 is disposed in the boundary portion B of the anastomosis portion In between the pancreas 100 and the jejunum 200, the drain tube 10 is caused to indwell the inside of a patient. Basically, in the boundary portion B, the cut surface 104 of the pancreas 100 and the facing surface 208 of the jejunum 200 are in contact with each other. However, a slight gap BS is generated between both of these. In addition, after the insertion planned region 12 indwells, the proximal side of the drain tube 10 is connected to the drain bag 50 set in the aspiration device 52 (refer to FIG. 5) outside the body.

If the biological tissue in the vicinity of the cut surface 104 generates the pancreatic juice (pj), the pancreas 100 causes the pj to be exuded from the cut surface 104 rather than causing the pj to flow to the main pancreatic duct 102. That is, a portion of the pj leaks to the gap BS of the boundary portion B between the pancreas 100 and the intestinal wall 202. In contrast, in the drain tube 10, the eight branch tubes 30 disposed in the boundary portion B cause the pj to flow from the branch side distal opening 31a to the branch lumen 31 by means of the capillary phenomenon. The pj flows into the main shaft lumen 21 via the branch lumen 31.

Therefore, the pj moves through the main shaft lumen 21 in the proximal end direction, and is drained to the drain bag 50 outside the body which is connected to the proximal side of the main shaft tube 20. That is, the pj of the main pancreatic duct 102 and the pj of the boundary portion B are drained out of the body by the atmospheric pressure (without applying the negative pressure) (refer to FIG. 4).

Furthermore, in a case where the pj exuded in the boundary portion B needs to be positively drained, the aspiration device 52 is operated. In this manner, the negative pressure (for example, −30 mmHg) corresponding to the positive pressure of the pj exuded from the main pancreatic duct 102 is applied to the main shaft lumen 21 via the set drain bag 50. The aspiration device 52 may apply the negative pressure steadily or intermittently, based on the settings of the operator.

In this manner, as illustrated in FIG. 5, the negative pressure is applied to the interlock cylindrical portion 41 from the proximal side of the main shaft tube 20, and the intermediate portion is deformed inward in the radial direction, thereby closing the intermediate lumen 42. In this case, in FIG. 5, the inner walls facing each other in the interlock cylindrical portion 41 come into contact with each other, thereby closing the intermediate lumen 42. Three or more circumferentially different locations in the interlock cylindrical portion 41 may be deformed inward, and the inner walls may come into contact with each other. In this manner, the intermediate lumen 42 may be closed. As a result, communication between the main shaft lumen 21 (between the distal side lumen 27 and the proximal side lumen 28) is blocked, and the pj no longer flows into the main shaft lumen 21 from the main pancreatic duct 102.

Accordingly, the negative pressure is applied from the drain bag 50 to the branch lumen 31 of the plurality of the branch tubes 30, and the pj leaking to the boundary portion B is promoted to flow from the branch side distal opening 31a into the branch lumen 31. Furthermore, the pj of the boundary portion B moves forward from the branch lumen 31 to the main shaft lumen 21 in the proximal end direction, and is accumulated in the drain bag 50 to which the negative pressure is applied. That is, the drain tube 10 can selectively and satisfactorily collect the pj leaking to the boundary portion B by applying the negative pressure to the proximal side of the main shaft lumen 21.

In addition, in an indwelling state of the drain tube 10, the pj generated by the biological tissue of the pancreas 100 mostly flows from the branch pancreatic duct 103 to the main pancreatic duct 102. Then, the pj flowing inside the main pancreatic duct 102 flows from the main shaft side distal opening 21a to the distal side lumen 27 of the main shaft lumen 21. In this manner, pressure (positive pressure) is applied from the distal side to the main shaft lumen 21. Under this pressure, the interlock cylindrical portion 41 opens the intermediate lumen 42, thereby being capable of flowing the pj (refer to FIG. 6).

That is, if the pj is accumulated in the main pancreatic duct 102, low pressure is applied to the interlock cylindrical portion 41 by the pj flowing from the main shaft side distal opening 21a, thereby generating the positive pressure. Then, the intermediate lumen 42 of the interlock cylindrical portion 41 is opened, thereby being capable of draining the pj of the main pancreatic duct 102.

In addition, in the interlock cylindrical portion 41, the negative pressure applied from the proximal side of the main shaft lumen 21 is released, and the elastic restoring force causes the intermediate lumen 42 to be opened again. In this manner, a configuration may be adopted in which the pj of the main pancreatic duct 102 can be drained.

After surgery, in the boundary portion B, the pancreas 100 and the jejunum 200 progressively adhere to each other. Then, if a certain period of time elapses after the surgery, the drain tube 10 is removed. At this time, the operator can smoothly detach the main shaft tube 20 and the branch tube 30 from the anastomosis portion In by simply moving the main shaft tube 20 rearward in the proximal end direction.

As described above, the drain tube 10 (medical tube 10) can satisfactorily drain the pj flowing from the main shaft side distal opening 21a of the main shaft tube 20, and the pj flowing from the branch side distal opening 31a of the branch tube 30 by causing the pj to flow through the main shaft lumen 21 in the proximal end direction.

Furthermore, the drain tube 10 has the flow path opening/closing mechanism 40. Accordingly, the negative pressure is applied from the proximal side of the main shaft lumen 21 further from the flow path opening/closing mechanism 40. In this manner, the interlock cylindrical portion 41 can close the main shaft lumen 21. The pj can be promoted to flow from the branch tube 30 by restraining the pj from flowing from the main shaft side distal opening 21*a*.

In addition, even under the negative pressure on the proximal side, the pj flowing from the main shaft side distal opening 21*a* pressurizes the main shaft lumen 21. Accordingly, the main shaft lumen 21 is brought into an open state, thereby being capable of draining the pj. In addition, the main shaft lumen 21 can be brought into a closed state again in response to the main shaft lumen 21 depressurized by the drain. Accordingly, the pj can be drained without applying the negative pressure load into the main pancreatic duct 102. Therefore, the drain tube 10 can more satisfactorily encourage recovery of a patient.

In this case, one main shaft lumen 21 is disposed inside the main shaft tube 20, and the flow path opening/closing mechanism 40 is disposed on the distal side further from the interlock portion of the branch tube 30. Accordingly, the flow path opening/closing mechanism 40 can switch opening/closing of the main shaft lumen 21 in the first site 24. In addition, the flow path opening/closing mechanism 40 is the interlocking cylindrical portion 41 which has a tubular shape and has the same diameter as that of the main shaft tube 20. Accordingly, the flow path opening/closing mechanism 40 can be easily manufactured, and can be installed at a desired position in the main shaft tube 20. Then, the interlock cylindrical portion 41 is more flexible than the wall portion of the main shaft tube 20. Accordingly, the interlock cylindrical portion 41 is bent inward in the radial direction by the negative pressure applied from the proximal side of the main shaft lumen 21, thereby being capable of satisfactory closing the main shaft lumen 21.

The drain tube 10 is not limited to the above-described configuration, and various configurations can be adopted. For example, instead of the branch tube 30, a side hole (lateral introduction portion, not illustrated) through which the outside of the main shaft tube 20 communicates with the main shaft lumen 21 may be disposed in the second site 25 of the main shaft tube 20, and the pj of the boundary portion B may be caused to flow from the side hole.

Hereinafter, other configurations of the drain tube 10 are described. In the following description, the same reference numerals will be given to configurations having the same configuration or the same functions as those of the drain tube 10 described above, and detailed description thereof will be omitted.

Figure 7A:
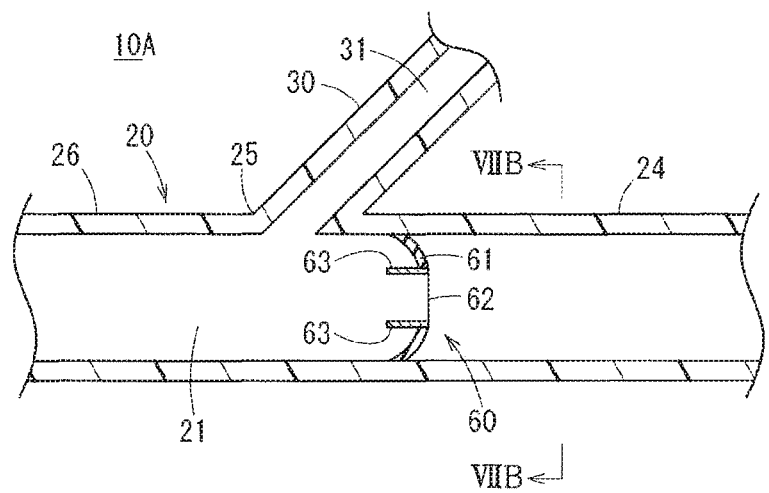
FIG. 7A is a side cross-sectional view illustrating an enlarged distal side of a medical tube in accordance with embodiments of the present disclosure.
Figure 7B:
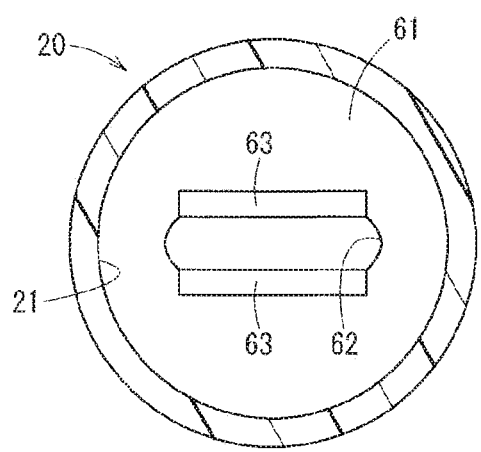
FIG. 7B is a cross-sectional view taken along line VIIB-VIIB in FIG. 7A in accordance with embodiments of the present disclosure.

A drain tube 10A (medical tube 10A) can be different from the drain tube 10 in that the drain tube 10A has a flow path opening/closing mechanism 60 which opens/closes the main shaft lumen 21 inside the main shaft tube 20, as illustrated in FIGS. 7A and 7B. In order to facilitate understanding of the drain tube 10A, FIG. 7A simply illustrates one branch tube 30 interlocking with the main shaft tube 20. However, as a matter of course, the branch tube 30 is not limited thereto.

For example, the flow path opening/closing mechanism 60 of the drain tube 10A has a diaphragm 61 interlocking with the inner surface configuring the main shaft lumen 21 and having the port 62, and a reinforcement body 63 disposed in an edge portion of the port 62.

In a side cross-sectional view taken along the shaft center of the main shaft tube 20, while forming a circular arc shape, the diaphragm 61 protrudes in the distal end direction from the inner surface of the main shaft tube 20 and inward in the radial direction. Then, in the diaphragm 61, the port 62 is disposed at the center position (shaft center of the main shaft tube 20) which protrudes most in the distal end direction. The diaphragm 61 is configured to be hard to some degree, and opens the port 62 in a normal state where the negative pressure is not applied from the proximal side of the main shaft lumen 21. On the other hand, the diaphragm 61 receives the negative pressure equal to or greater than a predetermined value from the proximal side of the main shaft lumen 21. In this manner, the diaphragm 61 is elastically deformed to the proximal side of the main shaft lumen 21 and inward in the radial direction. For example, a resin material for configuring this type of diaphragm 61 includes silicone rubber.

The reinforcement body 63 is formed in a plate shape, and a pair of the reinforcement bodies 63 interlocks with and is fixed to upper and lower edge portions of the diaphragm 61 configuring the port 62 so as to reinforce the edge portions. The axial length of the pairs of reinforcement bodies 63 is longer than the thickness of the diaphragm 61. The reinforcement body 63 may be harder or more flexible than the diaphragm 61.

The pair of reinforcement bodies 63 is separated from each other in a normal state, and sufficiently secures a flow path area of the main shaft lumen 21. Then, the respective reinforcement bodies 63 move close to and come into surface contact with each other, as the diaphragm 61 is elastically deformed inward in the radial direction and toward the proximal side. In this manner, it is possible to block the flow of the pj by more reliably closing the port 62. In addition, the pair of reinforcement bodies 63 can be expected to fulfill a role as a weight to promote the elastic deformation of the diaphragm 61 by applying the negative pressure from the proximal side of the main shaft lumen 21.

Figure 8A:
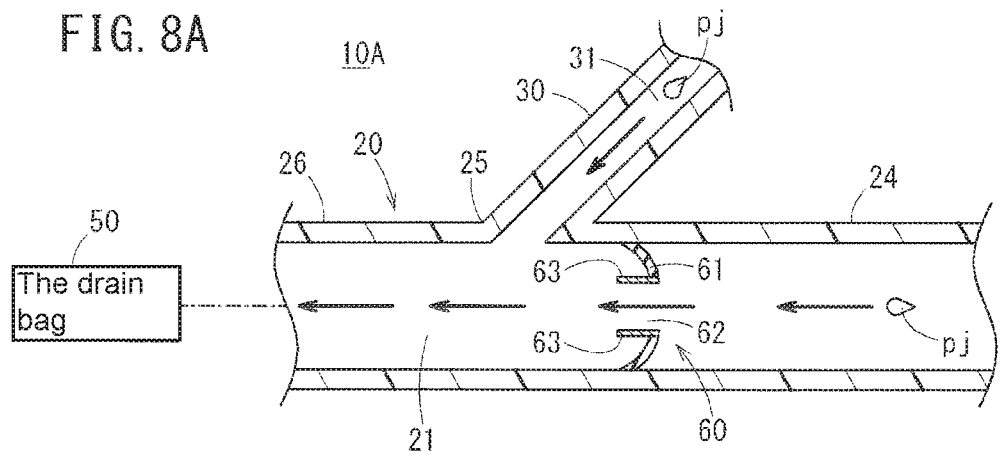
FIG. 8A is a side cross-sectional view illustrating an example where the pancreatic juice is drained in a normal state of the medical tube in FIG. 7A in accordance with embodiments of the present disclosure.

Similarly to the drain tube 10, the drain tube 10A described above indwells the boundary portion B between the pancreas 100 and the jejunum 200 (refer to FIG. 2A and FIG. 2B). As illustrated in FIG. 8A, in a normal state, the pj flows from the main pancreatic duct 102 to the main shaft lumen 21 via the main shaft side distal opening 21*a*. At this time, the diaphragm 61 of the flow path opening/closing mechanism 60 receives the positive pressure from the flowing pj. However, under this pressure, an open state of the port 62 is maintained.

Therefore, the drain tube 10A can drain the pj of the main pancreatic duct 102 to the drain bag 50 by causing the pj to satisfactorily flow in the proximal end direction. Similarly, the branch tube 30 causes the pj of the boundary portion B to flow, and drains the pj to the drain bag 50.

Figure 8B:
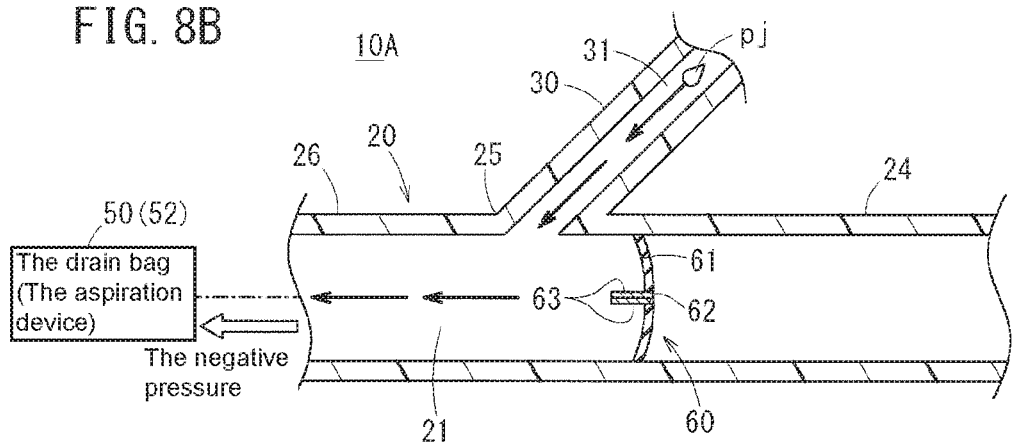
FIG. 8B is a side cross-sectional view illustrating an example where the pancreatic juice is drained in a state where the negative pressure is applied to the medical tube in FIG. 7A in accordance with embodiments of the present disclosure.

On the other hand, as illustrated in FIG. 8B, in a state where the negative pressure is applied from the drain bag 50 to the main shaft lumen 21, the diaphragm 61 is elastically deformed, and the pair of reinforcement bodies 63 is displaced inward in the radial direction. Then, the pair of reinforcement bodies 63 comes into surface contact with each other, thereby closing the main shaft lumen 21 of the first site 24. As a result, the negative pressure is applied to the branch lumen 31 of the branch tube 30 disposed in the boundary portion B. Accordingly, the flow of the pj leaking to the boundary portion B is promoted, thereby being capable of draining the pj to the drain bag 50.

Figure 8C:
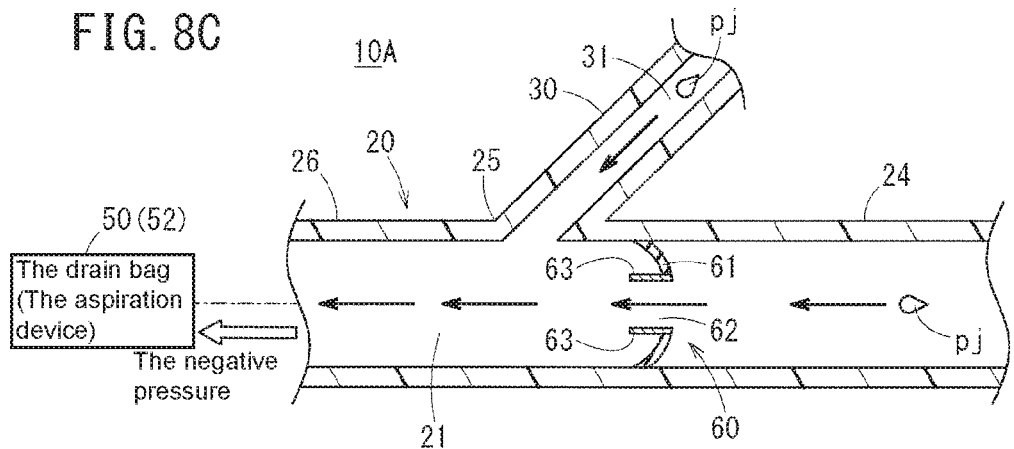
FIG. 8C is a side cross-sectional view illustrating an example where the pancreatic juice is drained in a state where the positive pressure is applied after the pancreas secretes the pancreatic juice from the state illustrated in FIG. 8B in accordance with embodiments of the present disclosure.

Then, as illustrated in FIG. 8C, even in a state where the negative pressure is applied to the main shaft lumen 21, the pj flowing from the main shaft side distal opening 21*a* pressurizes the main shaft lumen 21. Accordingly, the main shaft lumen 21 is brought into an open state, thereby being capable of draining the pj. In addition, the main shaft lumen 21 can be brought into a closed state again in response to the main shaft lumen 21 depressurized by the drain. Accordingly, the pj can be drained without applying the negative pressure load into the main pancreatic duct 102. Therefore, the drain tube 10A can more satisfactorily encourage recovery of a patient.

As described above, the drain tube 10A can also obtain an advantageous effect the same as that of the drain tube 10. In particular, in the drain tube 10A, the flow path opening/closing mechanism 60 is the diaphragm 61. Accordingly, the port 62 is opened in a normal state, thereby being capable of causing the main shaft lumen 21 to be in a communicating state. In addition, the negative pressure equal to or greater than a predetermined value is applied so that the main shaft lumen 21 is bent inward in the radial direction and the port 62 is closed, thereby being capable of simply closing the port 62.

The flow path opening/closing mechanism 60 is not limited to the above-described configuration. Various configurations can be adopted in which whereas the main shaft lumen 21 can be opened when the pressure equal to or smaller a predetermined value is applied to the main shaft lumen 21, the main shaft lumen 21 can be closed when the pressure greater than the predetermined value is applied to the main shaft lumen 21. For example, as illustrated in FIGS. 9A and 9B, the flow path opening/closing mechanisms 60A and 60B may have mutually different interlock positions of the reinforcement body 63 interlocking with the diaphragm 61. In addition, for example, the reinforcement body 63 may be formed in an arc shape in a cross section as in a flow path opening/closing mechanism 60C illustrated in FIG. 9C, or may be formed in a polygonal shape (triangular shape) in a cross section as in a flow path opening/closing mechanism 60D illustrated in FIG. 9D. Alternatively, the reinforcement body 63 may be formed in circular shape in a cross section as in a flow path opening/closing mechanism 60E illustrated in FIG. 9E, or may be formed in a semicircular shape in a cross section as in a flow path opening/closing mechanism 60F illustrated in FIG. 9F. Furthermore, for example, as in a flow path opening/closing mechanism 60G illustrated in FIG. 9G, in the diaphragm 61, the reinforcement body 63 may be disposed by protruding in the direction orthogonal to the shaft center of the main shaft tube 20. Alternatively, as in a flow path opening/closing mechanism 60H illustrated in FIG. 9H, the reinforcement body 63 may be disposed so as to tilt in the direction toward the shaft center of the main shaft tube 20 and in the proximal end direction.

Figure 10A:
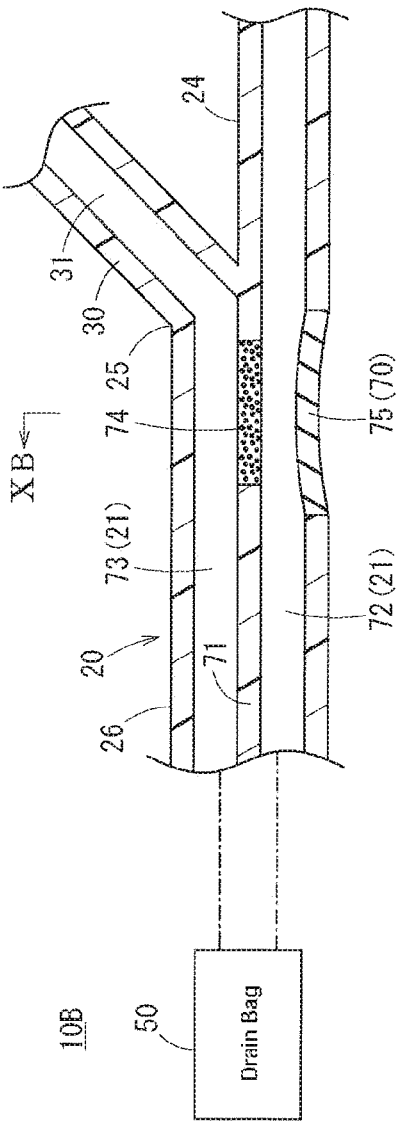
FIG. 10A is a side cross-sectional view illustrating an enlarged distal side of a medical tube in accordance with embodiments of the present disclosure.
Figure 10B:
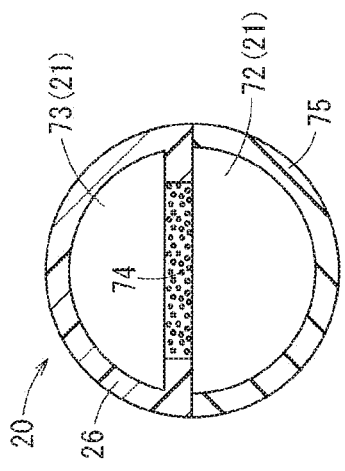
FIG. 10B is a cross-sectional view taken along line XB-XB in FIG. 10A in accordance with embodiments of the present disclosure.

Another drain tube 10B (medical tube 10B) is different from the drain tubes 10 and 10A in that the main shaft lumen 21 of the main shaft tube 20 configures a double lumen and one lumen has a flow path opening/closing mechanism 70, as illustrated in FIGS. 10A and 10B.

Specifically, the main shaft tube 20 includes a partition wall 71 extending along the shaft center portion, and the main shaft lumen 21 is independently divided into a first lumen 72 which communicates with the main shaft side distal opening 21*a* (refer to FIG. 3A), and a second lumen 73 which communicates with the branch lumen 31 of the branch tube 30. The first and second lumens 72 and 73 are formed in a semicircular shape in a cross-sectional view orthogonal to the shaft center of the main shaft tube 20. Then, the retention space of the drain bag 50 interlocking with the proximal side of the main shaft tube 20 communicates with both the first and second lumens 72 and 73.

In addition, a gas permeable wall 74 which allows gas permeation while blocking liquid permeation is disposed at an intermediate position of the partition wall 71. The gas permeable wall 74 may be disposed in any of the first to third sites 24, 25, and 26, or in the exposure planned region 14 of the main shaft tube 20. For example, the gas permeable wall 74 can employ a porous body configured to have fine pores by performing processing such as firing on a metal material or a resin material.

In addition, the main shaft tube 20 configuring the first lumen 72 has a semi-cylindrical portion 75 (deformable wall portion) functioning as the flow path opening/closing mechanism 70. The semi-cylindrical portion 75 is formed at a position overlapping the gas permeable wall 74 in the axial direction. The distal end, the proximal end, and both side edges of an elastic membrane are fixedly attached to a portion from which the wall portion of the main shaft tube 20 is cut out, thereby surrounding a portion of the first lumen 72. Whereas the semi-cylindrical portion 75 opens the first lumen 72 in a normal state, the semi-cylindrical portion 75 is elastically deformed inward in the radial direction by the negative pressure applied from the proximal side of the first lumen 72, thereby closing the first lumen 72. That is, the first lumen 72 is selectively switched between an open state and a closed state.

Similarly to the drain tubes 10 and 10A, the drain tube 10B described above indwells the boundary portion B between the pancreas 100 and the jejunum 200 (refer to FIGS. 2A and 2B). As illustrated in FIG. 10A, in a normal state, the pj flows from the main pancreatic duct 102 to the first lumen 72 via the main shaft side distal opening 21*a*. At this time, the semi-cylindrical portion 75 of the flow path opening/closing mechanism 70 receives the positive pressure from the flowing pj. However, under this pressure, an open state of the first lumen 72 is maintained. Therefore, the drain tube 10B can cause the pj of the main pancreatic duct 102 to smoothly flow in the proximal end direction, and can drain the pj to the drain bag 50.

In addition, the second lumen 73 can also cause the pj of the boundary portion B to flow through the branch side distal opening 31*a* and the branch lumen 31, and can drain the pj to the drain bag 50. At this time, the gas permeable wall 74 allows gas to flow to each other between the first lumen 72 and the second lumen 73. On the other hand, the gas permeable wall 74 blocks the flow of the pj.

Figure 11A:
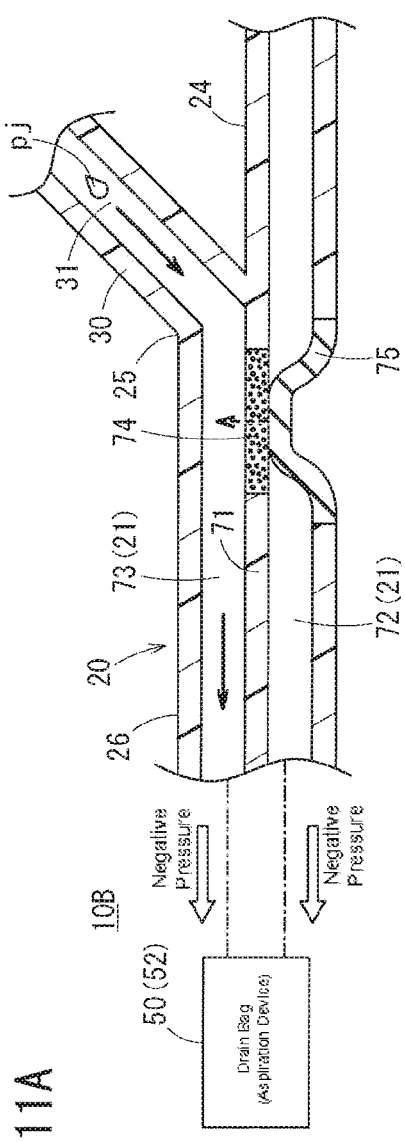
FIG. 11A is a side cross-sectional view illustrating an example where the pancreatic juice is drained in a state where the negative pressure is applied to the medical tube in FIG. 10A in accordance with embodiments of the present disclosure.

In addition, as illustrated in FIG. 11A, if the negative pressure is applied to the first and second lumens 72 and 73 from the drain bag 50, the semi-cylindrical portion 75 is elastically deformed and displaced inward in the radial direction, thereby closing the first lumen 72. In particular, the gas permeable wall 74 can also promote elastic deformation of the semi-cylindrical portion 75 facing the gas permeable wall 74 by applying the negative pressure from the second lumen 73 side. As a result, the negative pressure is applied to the branch lumen 31 of the branch tube 30 disposed in the boundary portion B. Accordingly, the pj leaking to the boundary portion B can be promoted to flow, and can be drained to the drain bag 50.

As described above, the drain tube 10B can also obtain an advantageous effect the same as that of the drain tubes 10 and 10A. In particular, the drain tube 10B has the first lumen 72 and the second lumen 73, and the flow path opening/closing mechanism 70 switches between an open state and a closed state of the first lumen 72. In this manner, it is possible to simply switch between draining the pj from the first and second lumens 72 and 73 under the atmospheric pressure and promoting drain of the pj from the second lumen 73. In addition, the gas permeable wall 74 disposed at the same axial position as the installation position of the flow path opening/closing mechanism 70 performs aspiration from the second lumen 73 side so that the semi-cylindrical portion 75 is shrunk inward. A closing degree of the semi-cylindrical portion 75 can be adjusted in accordance with a size of a hole portion on the gas permeable wall 74.

Figure 11B:
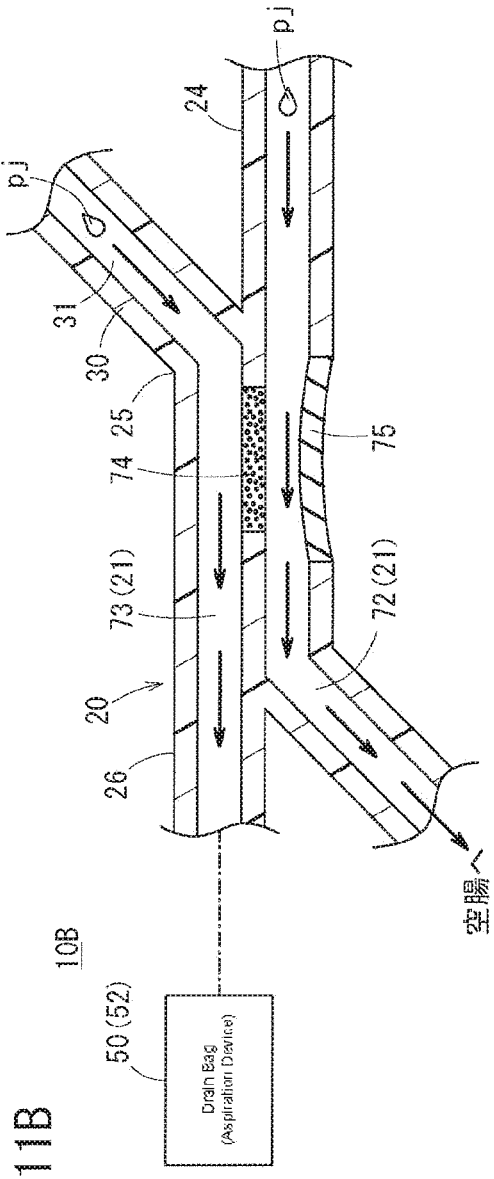
FIG. 11B is a side cross-sectional view illustrating an enlarged distal side of a medical tube in accordance with embodiments of the present disclosure.

As illustrated in FIG. 11B, the main shaft tube 20 of the drain tube 10B may have a structure which opens the proximal portion of the first lumen 72 inside the jejunum 200. In this manner, the pj of the main pancreatic duct 102 is drained into the jejunum 200, thereby being capable of flowing the pj from the jejunum 200 into the small intestine. Then, the second lumen 73 can drain only the pj leaking to the boundary portion B to the drain bag 50, and can analyze the pj.

In addition, although the illustration is omitted, the main shaft tube 20 may include the second lumen 73 in the shaft center portion, and may be configured to have a dual lumen type including the first lumen 72 so as to surround the second lumen 73 in the circumferential direction. Then, a structure may be employed as follows. The tubular gas permeable wall 74 is disposed at the intermediate position in the axial direction of the wall portion configuring the second lumen 73, and the tubular flow path opening/closing mechanism 70 (interlock cylindrical portion) is disposed at a facing position of the gas permeable wall 74 configuring the first lumen 72.

The present invention is not limited to the above embodiments. As a matter of course, various modifications can be made without departing from the gist of the present invention.

DESCRIPTION OF REFERENCE NUMERALS AND SIGNS 10, 10A, 10B: MEDICAL TUBE (DRAIN TUBE)
20: MAIN SHAFT TUBE
21: MAIN SHAFT LUMEN
21a: MAIN SHAFT SIDE DISTAL OPENING
24: FIRST SITE
25: SECOND SITE
26: THIRD SITE
30: BRANCH TUBE
31: BRANCH LUMEN
40, 60, 60A TO 60H, 70: FLOW PATH OPENING/CLOSING MECHANISM
41: INTERLOCK CYLINDRICAL PORTION
50: DRAIN BAG
52: ASPIRATION DEVICE
61: DIAPHRAGM
62: PORT
71: PARTITION WALL
72: FIRST LUMEN
73: SECOND LUMEN
74: GAS PERMEABLE WALL
75: SEMI-CYLINDRICAL PORTION
100: PANCREAS
104: CUT SURFACE
200: JEJUNUM
202: INTESTINAL WALL
208: FACING SURFACE
B: BOUNDARY PORTION
In: ANASTOMOSIS PORTION
pj: PANCREATIC JUICE

The invention claimed is:

1. A medical tube comprising:
an elongated main shaft tube that has a distal end and a proximal end, that has a distal opening on a distal side, and that internally has a lumen which communicates with the distal opening;
a lateral introduction portion that is disposed at an intermediate position in an axial direction of the main shaft tube, and that introduces a fluid to the lumen from a boundary portion which connects a plurality of biological organs to each other; and
a flow path opening/closing mechanism that is operable to be in a state of opening the lumen and to be in a state of closing the lumen, wherein the flow path opening/closing mechanism closes the lumen, when negative pressure is applied to the lumen on a proximal side further from flow path opening/closing mechanism, and opens the lumen, when positive pressure is applied to the lumen on a distal side further from the flow path opening/closing mechanism or when the negative pressure is released, and wherein the fluid is aspirated into the lumen via the lateral introduction portion by the negative pressure, and flows inside the main shaft tube in a proximal end direction.

2. The medical tube according to claim 1, wherein the lumen is disposed at one location inside the main shaft tube, and wherein the flow path opening/closing mechanism is disposed on the distal side further from the lateral introduction portion.

3. The medical tube according to claim 2, wherein the flow path opening/closing mechanism is more flexible than a wall portion of the main shaft tube, and both end portions are cylindrical portions fixed to the wall portion, and wherein the cylindrical portions close the lumen in such a way that the cylindrical portions are deformed so that inner walls thereof come into contact with each other when the negative pressure is applied.

4. The medical tube according to claim 2, wherein the flow path opening/closing mechanism is a diaphragm which is disposed on an inner surface of the main shaft tube configuring the lumen, and which has a port capable of opening/closing the lumen.

5. The medical tube according to claim 4, wherein a reinforcement body is disposed in the port.

6. The medical tube according to claim 1, wherein the lumen is divided into a first lumen communicating with the distal opening and a second lumen communicating with the lateral introduction portion so as to be independent of each other inside the main shaft tube, and wherein the flow path opening/closing mechanism opens/closes the first lumen.

7. The medical tube according to claim 6, wherein the main shaft tube has a partition wall which partitions the first lumen and the second lumen, wherein the partition wall has a gas permeable wall which allows gas to permeate and inhibits a liquid from permeating between the first lumen and the second lumen, wherein the flow path opening/closing mechanism is a deformable wall portion which is disposed at a position facing the gas permeable wall, and which configures a portion of the main shaft tube, and wherein the deformable wall portion closes the first lumen by coming into contact with the gas permeable wall when the negative pressure is applied.

8. The medical tube according to claim 7, wherein the lateral introduction portion is at least one branch tube which extends from the main shaft tube, which has a branch side distal opening, and which has the branch lumen communicating with the branch side distal opening.

9. A medical tube comprising:
an elongated main shaft tube that has a distal end and a proximal end, that has a distal opening on a distal side, and that internally has a lumen which communicates with the distal opening;
a lateral introduction portion that is disposed at an intermediate position in an axial direction of the main shaft tube, and that introduces a fluid to the lumen from a boundary portion which connects a plurality of biological organs to each other; and
a flow path opening/closing mechanism, wherein the flow path opening/closing mechanism closes the lumen, when negative pressure is applied to the lumen on a proximal side further from flow path opening/closing mechanism, and opens the lumen, when the negative pressure is released, and wherein the fluid is aspirated into the lumen via the lateral introduction portion by the negative pressure, and flows inside the main shaft tube in a proximal end direction.

10. The medical tube according to claim 9, wherein the flow path opening/closing mechanism comprises a diaphragm which is disposed on an inner surface of the main shaft tube configuring the lumen.

11. The medical tube according to claim 10, wherein the flow path opening/closing mechanism comprises two or more reinforcement bodies that have an interlock position that interlocks the diaphragm.

12. The medical tube according to claim 11, wherein each of the reinforcement bodies are formed on the diaphragm at a middle position of the reinforcement body.

13. The medical tube according to claim 11, wherein each of the reinforcement bodies are formed are formed in an arc shape.

14. The medical tube according to claim 11, wherein each of the reinforcement bodies are formed are formed in a polygon shape.

15. The medical tube according to claim 11, wherein each of the reinforcement bodies are formed are formed in a circular shape.

16. The medical tube according to claim 11, wherein each of the reinforcement bodies are formed are formed in a semicircular shape.

17. The medical tube according to claim 10, wherein each of the reinforcement bodies are formed by protruding, in a direction orthogonal to a shaft center of the main shaft tube.

18. The medical tube according to claim 10, wherein each of the reinforcement bodies are formed by protruding, in a second direction so as to tilt in the second direction toward a shaft center of the main shaft tube and tilt in a proximal end direction.

19. A medical tube comprising:
an elongated main shaft tube that has a distal end and a proximal end, that has a distal opening on a distal side, and that internally has a first lumen which communicates with the distal opening; and
a flow path opening/closing mechanism, wherein the flow path opening/closing mechanism closes the first lumen, when a first pressure is applied to the first lumen, and opens the first lumen, when the first pressure is released, and wherein the fluid is aspirated into the first lumen via a lateral introduction portion by the first pressure, and flows inside the main shaft tube to an end.

20. The medical tube according to claim 19, wherein elongated main shaft tube comprises a second lumen.

* * * * *